(12) United States Patent
Rauscher

(10) Patent No.: US 9,737,725 B2
(45) Date of Patent: Aug. 22, 2017

(54) ENHANCEMENT OF BIOLOGICAL FUNCTIONING BY THE USE OF ELECTROMAGNETIC AND MAGNETIC FIELDS

(71) Applicant: Elizabeth A. Rauscher, Apache Junction, AZ (US)

(72) Inventor: Elizabeth A. Rauscher, Apache Junction, AZ (US)

( * ) Notice: Subject to any disclaimer, the term of this patent is extended or adjusted under 35 U.S.C. 154(b) by 627 days.

(21) Appl. No.: 14/158,304

(22) Filed: Jan. 17, 2014

(65) Prior Publication Data

US 2014/0135566 A1 May 15, 2014

Related U.S. Application Data

(63) Continuation-in-part of application No. 13/096,232, filed on Apr. 28, 2011, now abandoned, which is a continuation-in-part of application No. 11/837,397, filed on Aug. 10, 2007, now Pat. No. 8,062,229.

(60) Provisional application No. 61/927,698, filed on Jan. 15, 2014, provisional application No. 61/349,740, filed on May 28, 2010.

(51) Int. Cl.
| *A61N 2/02* | (2006.01) |
| *A61N 1/32* | (2006.01) |
| *A61N 2/00* | (2006.01) |
| *A61B 5/00* | (2006.01) |

(52) U.S. Cl.
CPC ............ *A61N 2/02* (2013.01); *A61N 1/326* (2013.01); *A61N 2/004* (2013.01); *A61N 2/008* (2013.01); *A61B 5/40* (2013.01)

(58) Field of Classification Search
CPC .......... A61N 2/02; A61N 1/326; A61N 2/008; A61N 2/004; A61N 5/40
See application file for complete search history.

(56) References Cited

U.S. PATENT DOCUMENTS

| 849,653 A | 4/1907 | Bachelet |
| 1,164,356 A | 12/1915 | Kaiser |
| 2,517,325 A | 8/1950 | Lamb |
| 3,841,305 A | 10/1974 | Hallgren |
| 3,841,306 A | 10/1974 | Hallgren |
| 4,056,097 A | 11/1977 | Maass |
| 4,153,061 A | 5/1979 | Nemec |
| 4,182,315 A | 1/1980 | Vas et al. |
| 4,233,965 A | 11/1980 | Fairbanks |

(Continued)

FOREIGN PATENT DOCUMENTS

| DE | 2707574 | 8/1978 |
| EP | 0048451 | 3/1982 |
| EP | 0223354 | 9/1993 |

OTHER PUBLICATIONS

Becker, R.O., "New Light of Visualization", Cross Currents: The Promise of Electromedicine, The Perils of Electropollution, pp. 104-106.

(Continued)

*Primary Examiner* — Sean Dougherty
(74) *Attorney, Agent, or Firm* — Fish IP Law, LLC

(57) ABSTRACT

Apparatuses, systems and methods of treating a vertebrate organism via application of signals in a manner that enhances biological function. The signals applied can be produced by an electronic circuit, and can comprise magnetic fields emitted via one or more coil emitter devices.

20 Claims, 16 Drawing Sheets

(56) References Cited

U.S. PATENT DOCUMENTS

| | | | |
|---|---|---|---|
| 4,401,121 | A | 8/1983 | Rodler |
| 4,646,754 | A | 3/1987 | Scale |
| 4,654,574 | A | 3/1987 | Thaler |
| 4,693,238 | A | 9/1987 | Jerabek |
| 4,723,536 | A | 2/1988 | Rauscher et al. |
| 4,889,526 | A | 12/1989 | Rauscher et al. |
| 5,033,508 | A | 7/1991 | Laverty, Jr. |
| RE34,663 | E | 7/1994 | Seale |
| 5,476,481 | A | 12/1995 | Schondorf |
| 6,113,552 | A | 9/2000 | Shimazu et al. |
| 6,234,953 | B1 | 5/2001 | Thomas et al. |
| 7,988,613 | B2 | 8/2011 | Becker et al. |
| 8,062,229 | B2 | 11/2011 | Rauscher |
| 9,289,603 | B1* | 3/2016 | Giuffrida ............ A61B 5/1101 |
| 2004/0094021 | A1 | 5/2004 | Ludwig |
| 2006/0238194 | A1 | 10/2006 | Gleich |
| 2008/0021436 | A1 | 1/2008 | Wolpert et al. |
| 2008/0146865 | A1 | 6/2008 | Muntermann |
| 2009/0043188 | A1 | 2/2009 | Rauscher |
| 2009/0143725 | A1 | 6/2009 | Peyser et al. |
| 2009/0216068 | A1 | 8/2009 | Thomas et al. |
| 2010/0198101 | A1 | 8/2010 | Moore |
| 2010/0298624 | A1 | 11/2010 | Becker |
| 2011/0082384 | A1 | 4/2011 | Harte et al. |
| 2011/0105916 | A1 | 5/2011 | Rhodes |
| 2011/0125203 | A1* | 5/2011 | Simon ................ A61N 1/40 607/2 |
| 2011/0190569 | A1* | 8/2011 | Simon ................ A61N 1/18 600/26 |
| 2013/0184792 | A1* | 7/2013 | Simon ................ A61N 1/36025 607/115 |
| 2013/0317580 | A1* | 11/2013 | Simon ................ A61N 1/40 607/115 |

OTHER PUBLICATIONS

Bise, W.L. et al., "Multiple Extremely Low Frequency Magnetic and Electromagnetic Field Effects on Human Electroencephalogram and Behavior", Annual Review of Research on Biological Effects of Electromagnetic Fields from the Generation Delivery & Use of Electricity, US National Institute of Environmental Health Sciences, Sep. 13-17, 1998.

Kroening, R. et al. "Magnetic Control of Low Back Pain", Bulletin of the American Physical Society, 1989 Annual Join APS/AAPT Meeting, Jan. 15-19, 1989, San Francisco, CA.

Rauscher, E.A. et al. "Relaxation of Gauge Invariant Condition of ELF and VLF Phenomena and their Implications for Magnetic and Electromagnetic Wave Transmissions", Bulletin of the American Physical Society, 1989 Annual Join APS/AAPT Meeting, Jan. 15-19, 1989, San Francisco, CA.

Rauscher, E.A. et al. "Completely Chaotic Systems and Complex Logic Equations", Bulletin of the American Physical Society, 1989 Annual Join APS/AAPT Meeting, Jan. 15-19, 1989, San Francisco, CA.

Rauscher E.A. et al., "Magnetic Flux Control of Low Back Pain", Proceedings of the Associate of rth Advancement of Medical Instrumentation (AAMI), May 13-17, 1989, St. Louis, MO.

Rauscher E.A., "Pulsed Magnetic Field Control of Low Back Pain", Department of Physics and Astronomy Colloquium, Northwestern Universtiy, Mar. 10, 1993, Evanston, IL.

Rauscher E.A. et al., "Pulsed Magnetic Field Treatment of Chronic Back Pain", BEMS 23rd Annual Meeting, Jun. 10-14, 2001, St. Paul, MN.

Rauscher E.A. et al., "Degranulation of In Vivo Rat Brain Mast Cells by Exposure to External Pulsed Magnetic Fields", Annual Review of Research on Biological Effects of Electromagnetic Fields from the Generation Delivery & Use of Electricity, US National Institute of Environmental Health Sciences, Sep. 13-17, 1998.

Rauscher E.A. et al., "Health, Healing and Medicine", Tecnic Research Laboratory and Medicine Electronics, Oct. 1, 1985.

Rauscher E.A., "Probing into Control Mechanisms in Cellular Healing Processes: San Francisco Initiative", Planetary Associate for Clean Energy Newsletter, Feb. 1981, p. 8.

Rauscher E.A., "Closed Cosmological Solutions to Einstein's Field Equations", Lettere Al Nuovo Cimento, Apr. 15, 1972, vol. 3, No. 16, pp. 661-665.

Rauscher E.A., "Magnetic Field Interaction with Macro Biological Systems With Application to Effects on Physiology and Consciousness in Humans", International Conference on Energy Medicine, Feb. 27-Mar. 1, 1987, Madras.

Rauscher E.A., "Environmental Magnetic & Electromagnetic Field Monitoring: An Examination of Harmful, Benign & Beneficial Effects of ELF, VLF, LF & RF Fields on Biological Systems", The Ninth Annual International Symposium on Man and His Environment in Health and Disease, Feb. 28-Mar. 3, 1991, Dallas, TX.

Rauscher E.A., "Response of Physiological Parameters to Low Frequency and Low Intensity of Pulsed Magnetic Fields", The Ninth Annual International Symposium on Man and His Environment in Health and Disease, Feb. 28-Mar. 3, 1991, Dallas, TX.

Rauscher E.A., "Response of Physiological Parameters to Low Frequency and Low Intensity Pulsed Magnetic Fields and the Effects on Human Consciousness", The 31st Annual US Psychotronics Conference, Jul. 15-18, 2005, Columbus, OH.

Van Bise, W.L. et al., "Nonsupoerconducting Systems for Detecting and Analyzing Low Intensity Pure Magnetic Field", Bulletin of the American Physical Society, 1989 Annual Join APS/AAPT Meeting, Jan. 15-19, 1989, San Francisco, CA.

Wewers M.E. et al., "A Critical Review of Visual Analogue Scales in the Measurement of Clinical Phenomena", Research in Nursing & Health, 1990, vol. 13, pp. 227-236.

* cited by examiner

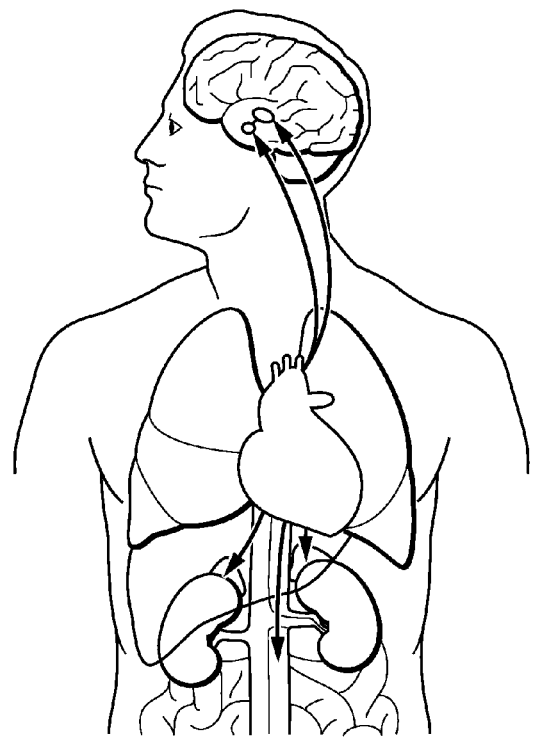
FIG. 8
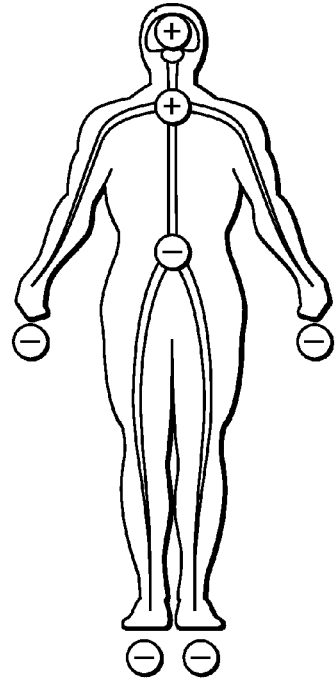
FIG. 9a
FIG. 10b
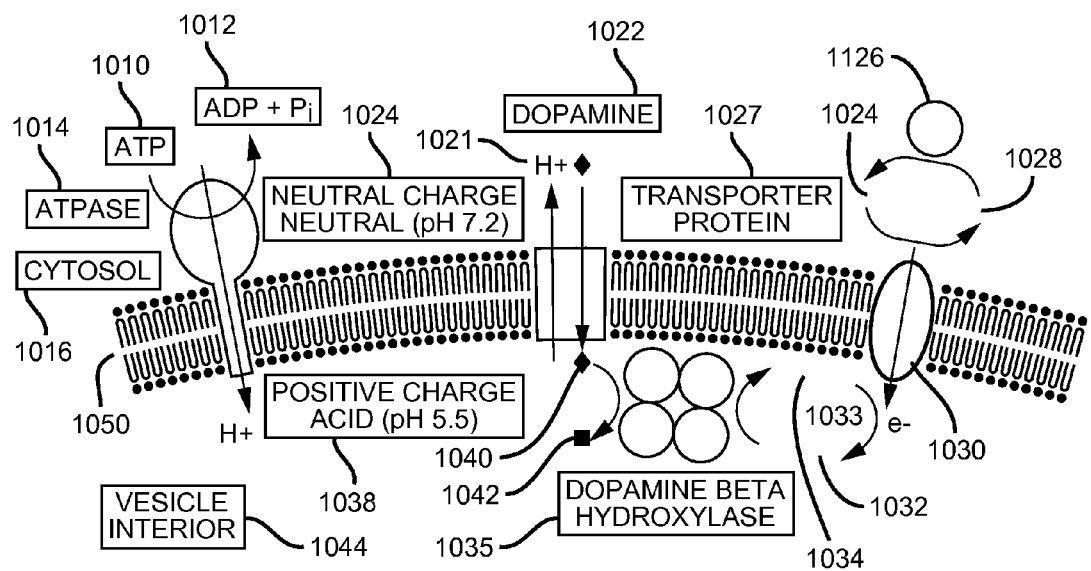

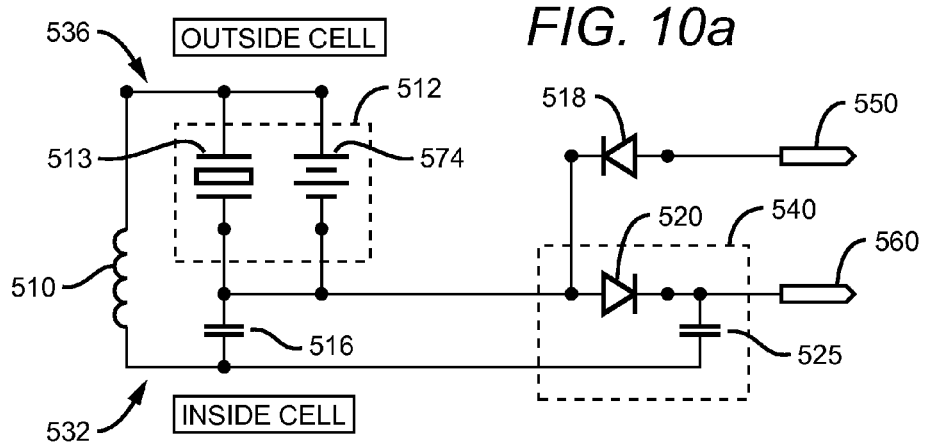
FIG. 10a
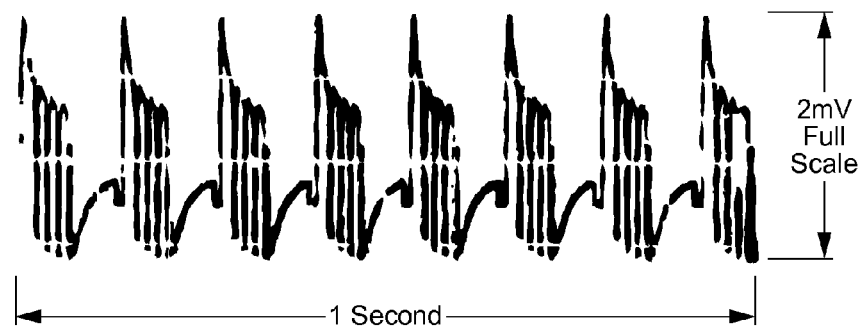
FIG. 11
FIG. 12
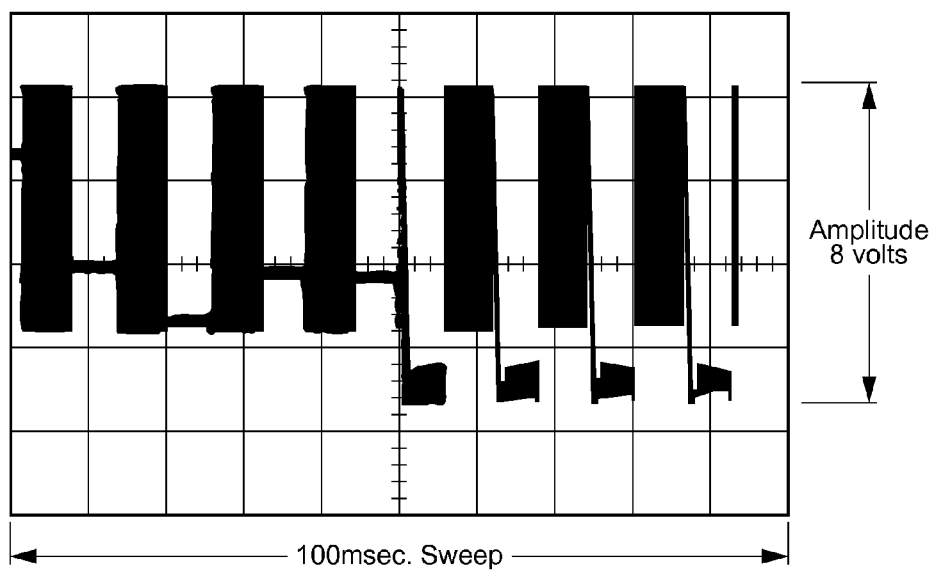

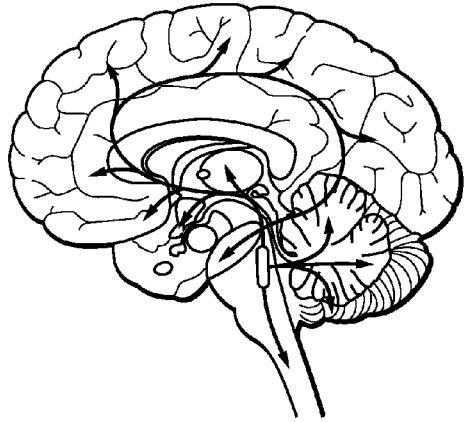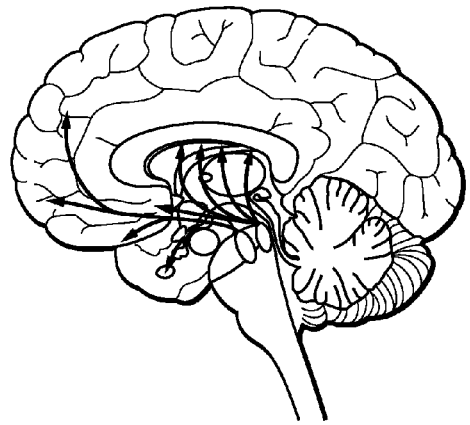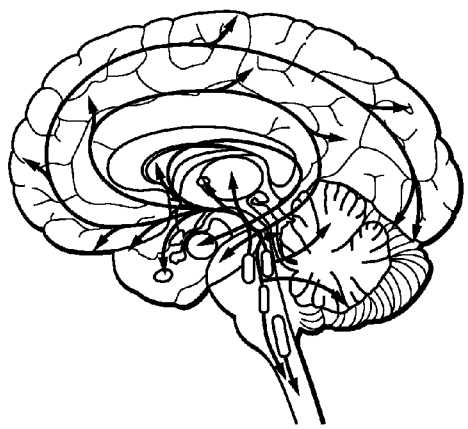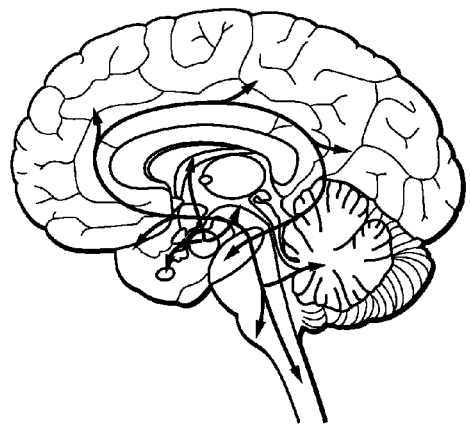
FIG. 15

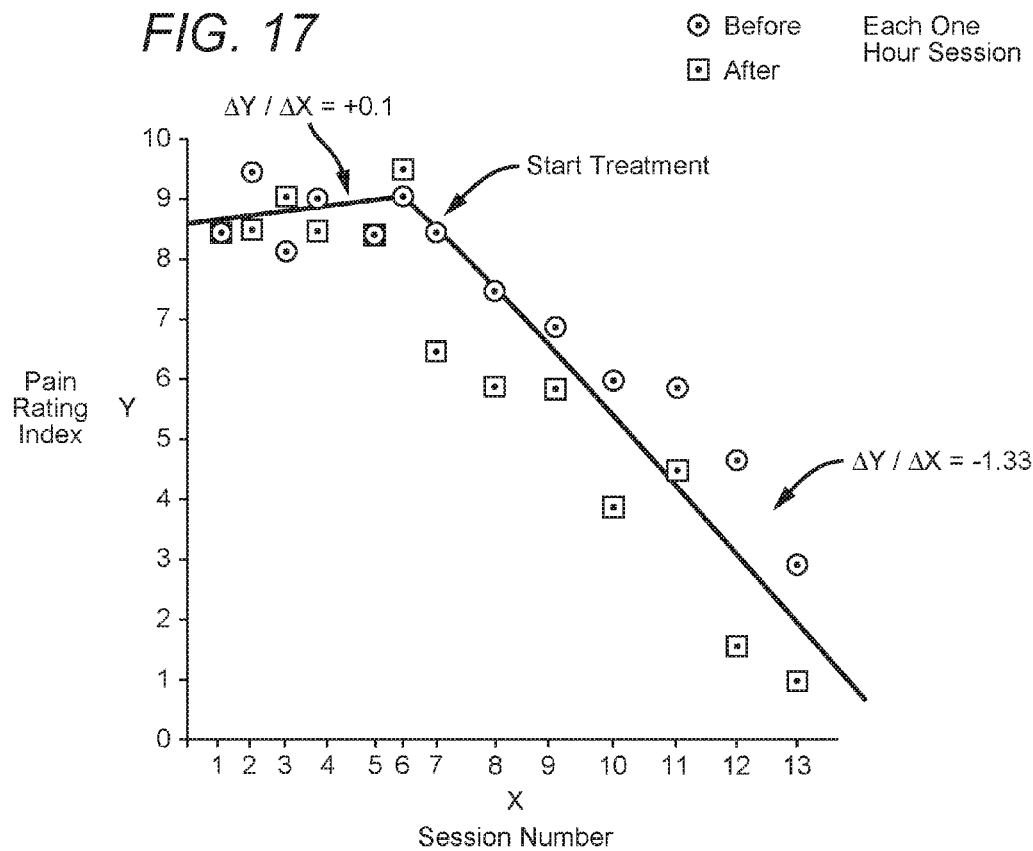
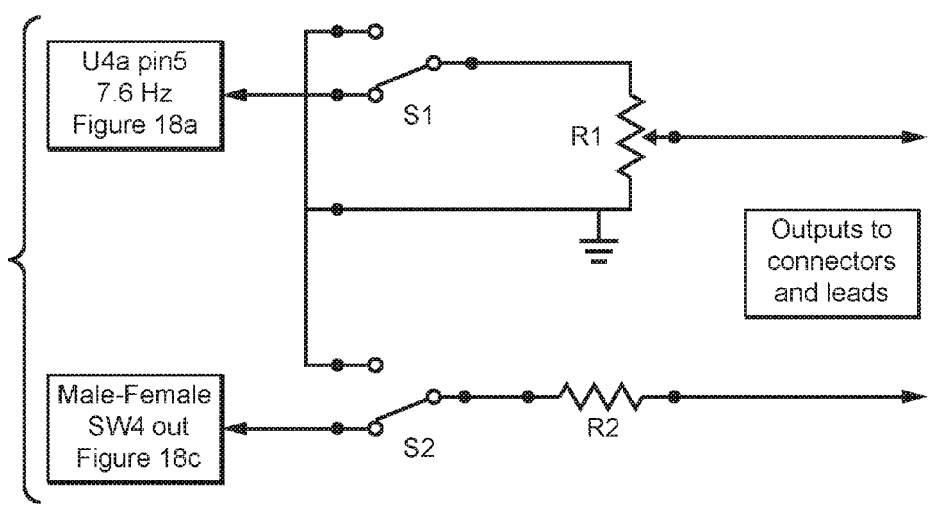

ENHANCEMENT OF BIOLOGICAL FUNCTIONING BY THE USE OF ELECTROMAGNETIC AND MAGNETIC FIELDS

This application claims the benefit of priority of U.S. Provisional Application No. 61/927,698, filed on Jan. 15, 2013, and is a continuation-in-part of co-pending U.S. patent application Ser. No. 13/096,232, filed on Apr. 28, 2011, which claims priority to U.S. Provisional Application No. 61/349,740, filed May 28, 2010. U.S. patent application Ser. No. 13/096,232 is also a continuation-in-part of U.S. patent application Ser. No. 11/837,397, filed Aug. 10, 2007, now issued U.S. Pat. No. 8,062,229.

These and all other publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is the enhancement of biological function through the application of magnetic fields.

BACKGROUND

The following description includes information that may be useful in understanding the present invention. It is not an admission that any of the information provided herein is prior art or relevant to the presently claimed invention, or that any publication specifically or implicitly referenced is prior art.

The nervous system is responsible for an organism's perception of the world. It interprets information external to the organism and converts it into electrochemical signals that are then interpreted by the brain. Of particular importance for this application is the nervous system's response to pain and discomfort.

Pain is an unpleasant feeling that is caused by intense or damaging stimuli. Similar to the way an organism interprets tactile sensations, painful stimuli are received and then transmitted in the form of electrical signals to the brain where they are interpreted. When a stimulus is sufficient to cause actual or potential damage to the body, the brain interprets that stimulus as pain and creates a negative feeling that ranges in intensity depending on the severity of the stimulus.

Pain can be brief or enduring. In some, enduring pain can be disruptive to an otherwise normal life, leading to complications such as depression or job loss. Thus providing relief to sufferers of chronic pain is extremely important to improve that person's quality of life.

Efforts have been made in the past to develop ways to reduce pain by applying electrical signals to the body. For example, in U.S. Pat. No. 5,476,481 to Schöndorf, a transcutaneous electrical nerve stimulation (TENS) device is described. To use the device, electrodes are placed on opposite sides of the target tissue and an electrical signal is applied. One electrode is positive and the other is negative, and an electrical signal comprised of multiple super-imposed frequencies is applied to the tissue traveling from the positive to the negative electrode.

A problem with Schöndorf's system, however, is that electrical signals dissipate when passing through the body. The target tissue acts as a continuous resistor, and the farther the signal travels through the tissue, the more resistance it will encounter, thus reducing the effectiveness of the therapy. Schöndorf attempts to address this issue, and the issue of applying the signal to only one side of the tissue, by periodically reversing the polarity of the positive and negative electrodes. Unfortunately, the signal is still reduced as a function of depth leaving the most central areas of tissue without sufficient stimulation.

Another problem with Schöndorf is that applying a varying electrical signal directly to the body will not electromagnetically induce current in conductive materials within the body. An electrical signal will pass current through a target tissue, but will not achieve this effect. Thus, electrical signals are limited in terms of depth of penetration and inability to electromagnetically induce current in conductive materials within the body.

Thus, there is still a need for improved devices, systems, and methods to improve biological function.

SUMMARY OF THE INVENTION

The inventive subject matter describes apparatuses, systems and methods of improving biological function of a vertebrate organism. In some contemplated methods, magnetic fields are applied to organisms, especially humans, and when applied to various locations at selected frequencies with selected duty cycles (e.g., approximately 10% (i.e., between 9-11%, inclusive), approximately 15%, approximately 25%, approximately 33.3%, approximately 50%, approximately 75%, between 0-25%, between 5-25%, between 10-75%, between 15-25%, between 20-40%, between 25-40%, between 35-55%, between 45-75%, etc.), the magnetic fields can improve biological function (e.g., promote pain reduction and relaxation). Viewed from another perspective, a method of the inventive subject matter described herein can utilize an electric circuit to generate and apply multiple, concurrent, superimposed, non-phase-locked signals. The signals can be applied at physiologically acceptable intensities and duty cycles, to a vertebrate organism such that the signals entrain that organism's tissue (e.g., to cause the target tissue's natural rhythms to synchronize with the resulting frequency of the applied magnetic field). The superimposed signals can be selected to produce a plurality of additional intermodulated signals.

A method of the inventive subject matter can implement at least one electronic circuit to generate signals having desired frequencies. The electronic circuit preferably generates at least two signals, with the first signal having a different frequency than the second, and can optionally generate a third signal having yet another different frequency.

Generated signals can be superimposed in the electronic circuit and transmitted from the electronic circuit to devices capable of receiving the signals. The devices can be, inter alia, coil emitters capable receiving a signal and emitting a magnetic field based on the received signal. The magnetic field the device generates can be applied to an organism's body. At least one of the devices can have a positive direct current bias, and at least one a negative direct current bias. The magnetic fields can be applied to the organism at physiologically acceptable intensities and duty cycles such that the signals entrain the target tissue. In some aspects of the inventive subject matter, the devices can compose multi-coil arrays. Additionally or alternatively, the devices can be comprised of multiple internal coils.

In this context, "duty cycle" is the percent of one cycle that a signal spends in an active state. Thus, duty cycle is the amount of time spent active in seconds divided into the period of the signal in seconds multiplied by 100. Time active can be the amount of time the signal spends above a rest state, or it can include the amount of time the signal spends above a particular voltage threshold set higher than the rest level.

Placement of the devices is important to proper implementation of some aspects of the inventive subject matter. For example, while not limiting to the scope of the inventive subject matter, a device having a positive direct current bias can be placed on the back of the neck over or near the C7 vertebra (i.e., within two vertebrae thereof) of a human being, targeting tissue in that area including tissue of the hypothalamic-pituitary axis. The negative direct current biased device or devices can then be placed on areas of the body where the patient has experienced pain or discomfort, thus targeting those tissues.

When a magnetic field is applied to the body, the tissues of the patient can be entrained and electromagnetic induction can occur in the body in a manner that, among other things, promotes health, subjectively relieves pain, relaxes, improves mood, reduces inflammation, prevents or treats osteoporosis, prevents or treats depression, anxiety, or other psychological maladies, enhances cardiac function, or brings about any other desired effect. The time required to achieve these results can be determined based on one or more characteristics of the patient and the desired effect, for example, height, gender e.g., (female, male, intersex) age, weight, type of pain, level of pain, symptoms, signs, etc.

Magnetic fields are also capable of penetrating deeper into an organism's tissue than an electrical current, and are additionally capable of causing electromagnetic induction. For these reasons, magnetic field application can be capable of creating effects that application of electric current may be unable to produce.

One of the frequencies can be selected from the list comprising or consisting of some or all of 7.6 Hz+/−2 Hz, 70.25 Hz+/−0.25 Hz, 71.25 Hz+/−0.25 Hz, and 3040 Hz+/−10 Hz, approximately 7.6 Hz, approximately 70.25 Hz, approximately 71.25 Hz, approximately 3040 Hz, a range of frequencies between 3.2-7.6 Hz, a range of frequencies between approximately 3.2-7.6 Hz, a range of frequencies between 7.6-9.4 Hz, a range of frequencies between approximately 7.6-9.4 Hz, a range of frequencies between 70.25-71.25 Hz, a range of frequencies between approximately 70.25-71.25 Hz, a range of frequencies between 3000-4000 Hz, and a range of frequencies between approximately 3000-4000 Hz. Additionally or alternatively, some or all frequencies (e.g., two, three, four, five) can be selected from the list comprising or consisting of some or all of 3.2 Hz+0.6 Hz/-0.1 Hz, 7.6 Hz+/−2 Hz, 9.41 Hz+/−2 Hz, 70.25 Hz+/−0.25 Hz, 71.25 Hz+/−0.25 Hz, and 3040 Hz+/−10 Hz, approximately 3.2 Hz, approximately 7.6 Hz, approximately 9.4 Hz, approximately 70.25 Hz, approximately 71.25 Hz, approximately 3040 Hz, a range of frequencies between 3.2-7.6 Hz, a range of frequencies between approximately 3.2-7.6 Hz, a range of frequencies between 7.6-9.4 Hz, a range of frequencies between approximately 7.6-9.4 Hz, a range of frequencies between 70.25-71.25 Hz, a range of frequencies between approximately 70.25-71.25 Hz, a range of frequencies between 3000-4000 Hz, and a range of frequencies between approximately 3000-4000 Hz. For example, a method of the inventive subject matter can comprise targeting two or more signals to affect Purkinje cells of an organism or any relevant excitable tissues.

Thus, through very precise application of electromagnetic fields, the amount of pain the human body perceives can be dramatically reduced. To achieve the goal of relaxation and reduced pain, an electromagnetic field can be applied to specific parts of the body. In addition, the frequency of the field can advantageously be closely controlled so as to bring about desirable results.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 8 shows a relationship between the hypothalamic pituitary axis and some biological functions of the human body.

FIG. 9a displays a DC bias polarity of the body and limbs.

FIG. 10a models communications between cells and the nervous system as a circuit diagram of an ultra-low power transceiver.

FIG. 10b is a diagrammatic representation of a vesicular membrane with integrated proteins performing transport functions.

FIG. 11 shows the output of an embodiment of the inventive subject matter for the intermix of 7.6 Hz and 70.25 Hz for a one second trace and amplitude of 2 mV in the time domain.

FIG. 12 shows the time domain for an embodiment of the inventive subject matter having the intermix of 7.6 Hz and 70.25 Hz and 3040 Hz biologically active frequencies for 100 ms sweep end to end and an amplitude of 8 V.

FIG. 15 shows the neurotransmitters norepinephrine, dopamine, serotonin, and histaminee and their pathways in the brain.

FIG. 17 shows a graph of pain rating index versus the number of sessions a patient is treated by an embodiment of the inventive subject matter.

FIG. 18c1-2 show circuit diagrams of a therapy countdown timer and power switching controls of an embodiment of the invention.

FIG. 18e shows a diagram that intermixes the 7.6 Hz frequency and Male/female frequencies from FIGS. 18a and 18c1-2.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figure 1:
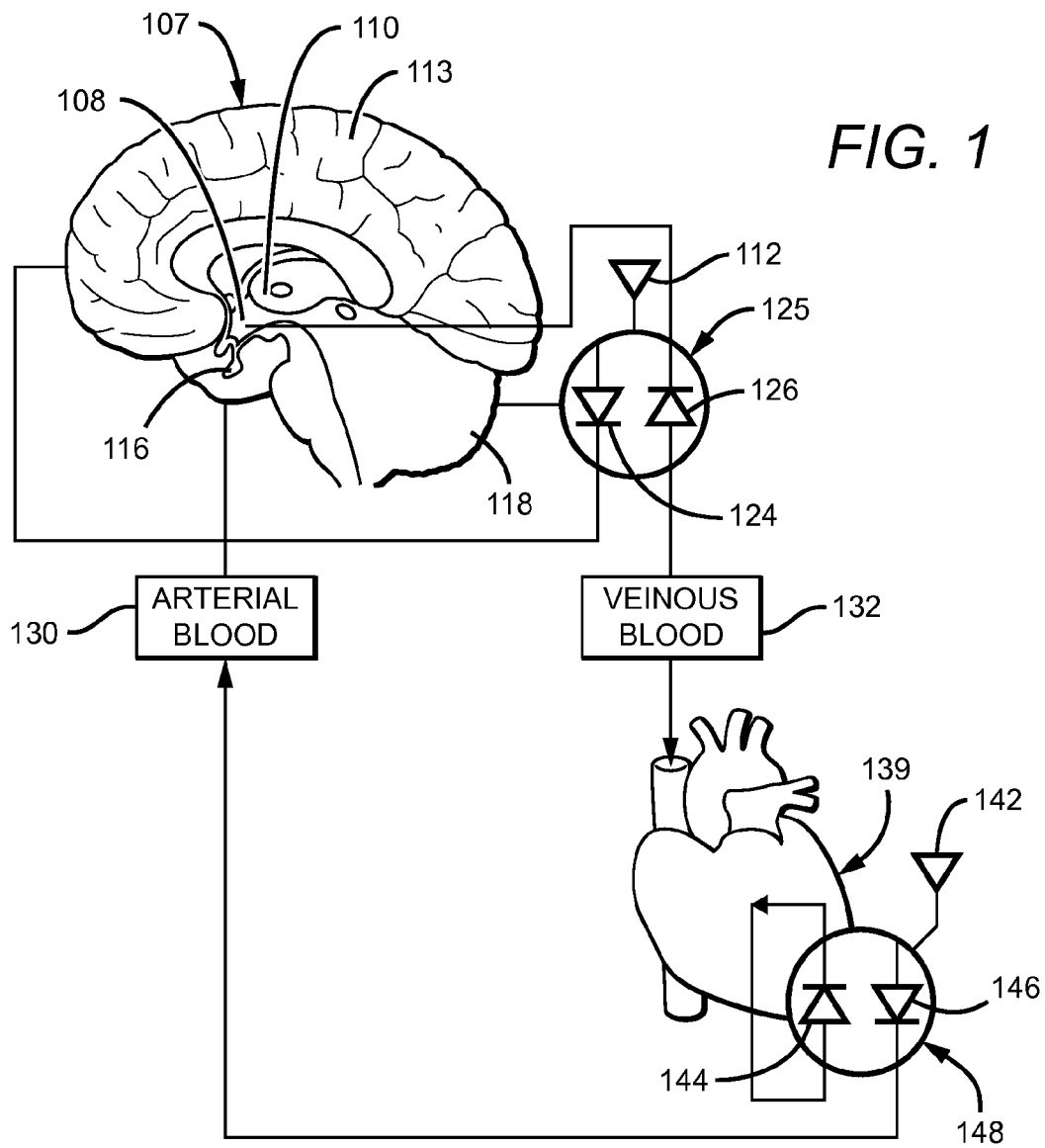
FIG. 1 illustrates the electrical activity of the brain and the heart and their interconnection.

FIG. 1 illustrates the electrical activity of a brain 107 and a heart 139 and their interconnection. The Purkinje process in the cerebellum 118 is represented by a Purkinje process diode array representation 125 comprising or consisting of a forward biased diode 126 and a back biased diode 124, the combination of which controls and rectifies electrical and paramagnetic signals between the brain 107 and the heart 139. The forward biased diode 126 connects to the hypothalamic-pituitary axis (HPA) (the hypothalamus being 110, and pituitary being 116). The antenna 112 of the Purkinje process diode array representation 125 can receive signaling from internal and external electromagnetic and other environmental sources. The endocardium Purkinje process is also represented by the diode array 148 consisting of a forward biased diode 144 and a back biased diode 146, the combination of which rectify electrical and paramagnetic signals. The antenna 142 of the endocardium Purkinje process representation reads in signaling primarily from the brain. Afferent paramagnetic read-write signaling moves from the heart 139, and diodes process 148 through arterial blood 130 to the brain. Veinous blood 132, paramagnetic from the brain signaling, moves from the read-write signaling from the Purkinje process diode array representation 125 to the heart 139, thereby completing an informational circuit.

Figure 2:
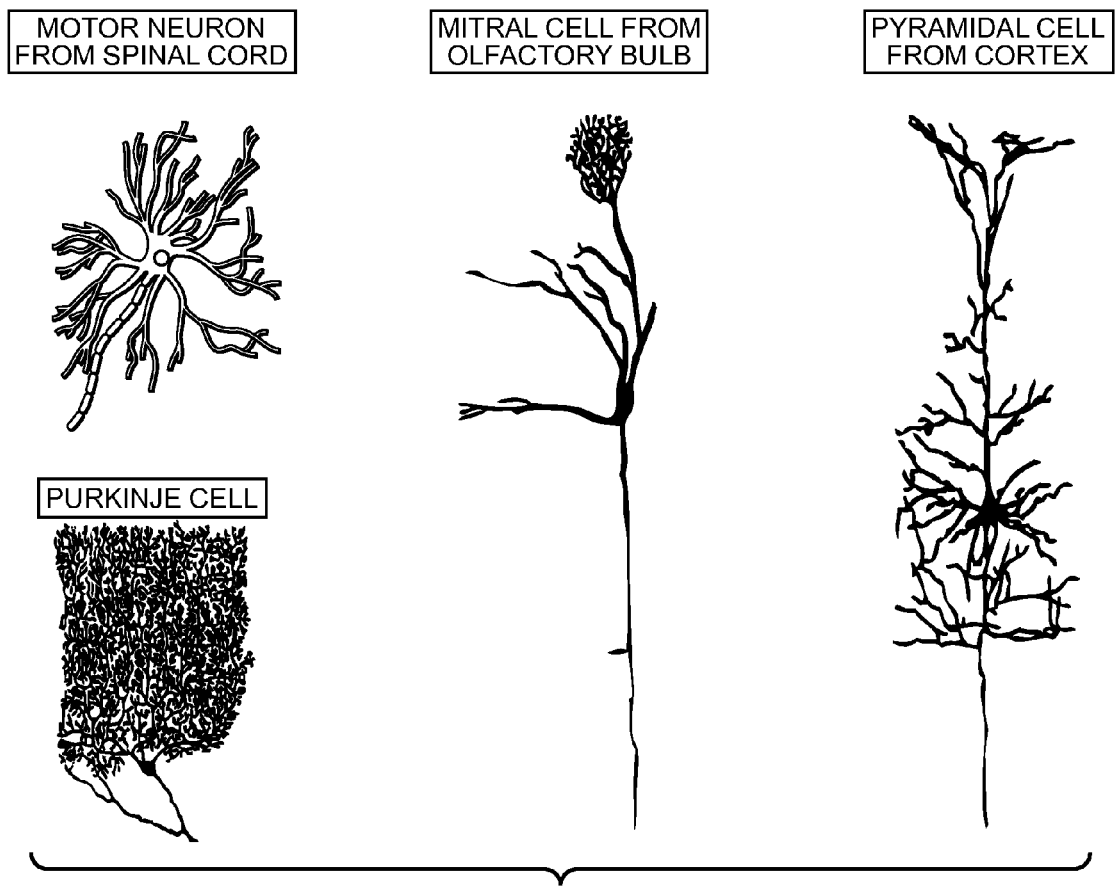
FIG. 2 displays cell structures for comparison to Purkinje cells.

FIG. 2 shows different cell structures for comparison to a Purkinje cell, including: a motor neuron from the spinal cord, a mitral cell from the olfactory bulb, and a pyramidal cell from the cortex.

Figure 3:
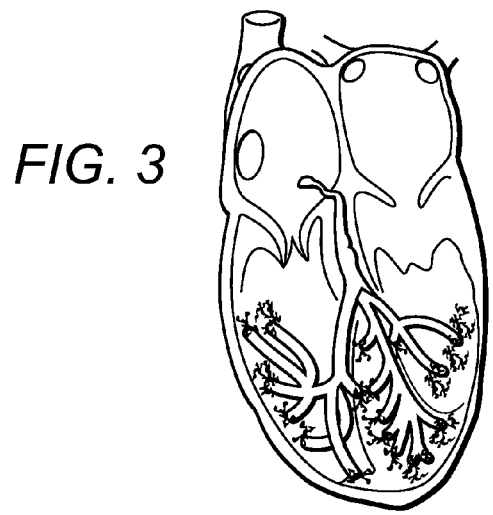
FIG. 3 illustrates a human heart having Purkinje cells.
Figure 4:
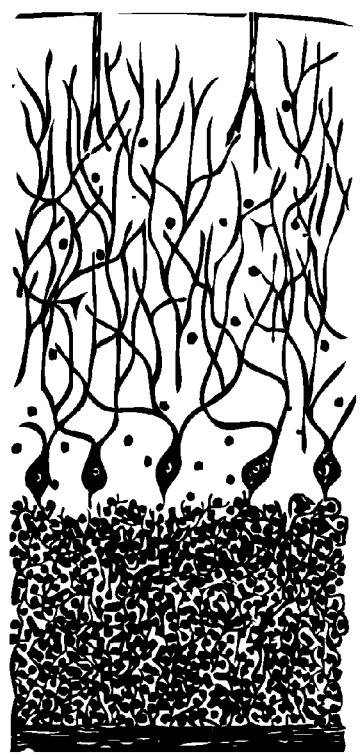
FIG. 4 shows the detailed structure of the Purkinje process in the cerebellum.

In FIG. 3, the structure of a heart having Purkinje fibers is illustrated. FIG. 4 illustrates the detailed structure of the Purkinje process in the cerebellum. The external gray or cellular matter comprises Purkinje fibers (top portion), the corpuscles of Purkinje (bulbous middle area), and act as a diode action on the internal layer (bottom portion) which acts as a semiconductor substrate layer standing on the white substrate layer (bottom).

Figure 5:
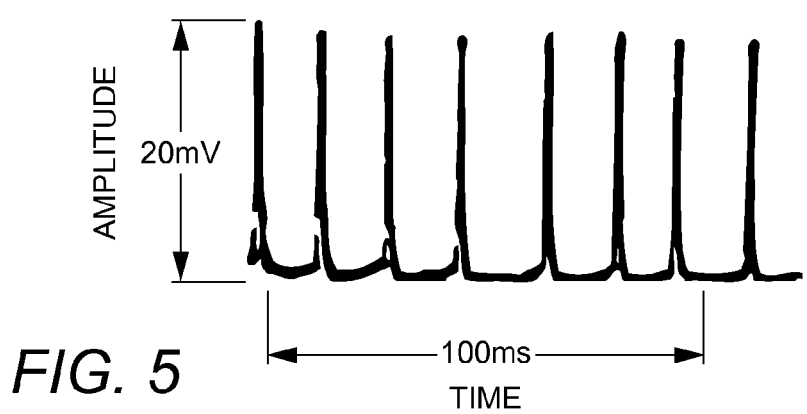
FIG. 5 shows the signaling output of Purkinje cells of the brain for an amplitude of 20 mV for a 100 ms trace of a frequency of approximately 7.4-7.6 HZ.

FIG. 5 illustrates a signaling output of the Purkinje cells of the brain having an amplitude of 20 mV for a 100 ms trace with a frequency of about 7.4-7.6 HZ.

Figure 6:
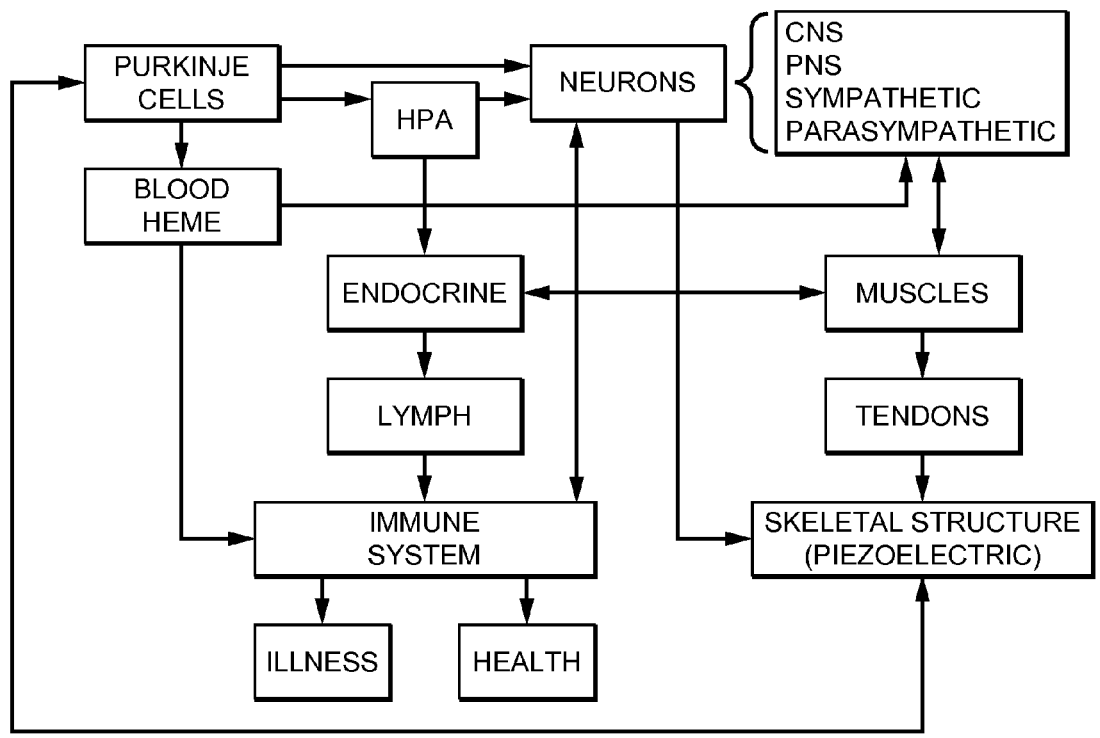
FIG. 6 is a flow chart generalizing the electromagnetically coupled processes and systems of the human body.

FIG. 6 is a generalized flow chart of the electromagnetically coupled processes and systems of the human body. The master I/O electromagnetic system, the Purkinje cells, encode and decode the paramagnetic properties of the blood heme, and relay information to the neuronal process. The neurons are divided into the CNS, PNS, sympathetic and parasympathetic systems. These systems feed back to the blood heme, which controls the endocrine system, the lymphatic system, and regulates the immune system. The blood heme neural system in turn feeds into muscles, tendons, and the piezoelectric skeletal structure while also providing bio-feedback to the endocrine system and its substructures.

Figure 7:
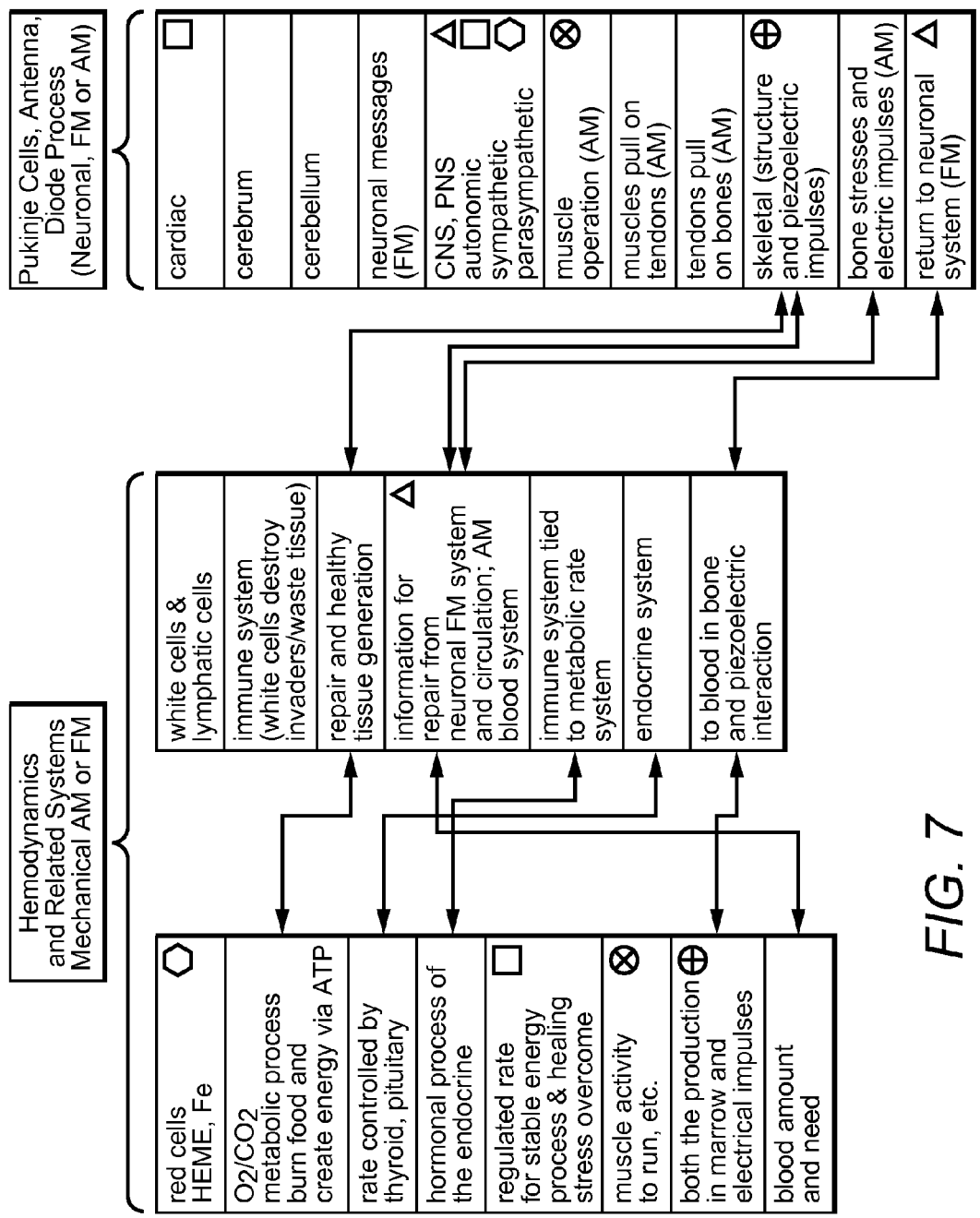
FIG. 7 shows detailed diagrams of how the hemodynamic and related systems, and the Purkinje cells, antenna, and diode processes interact and relate.

FIG. 7 is a more detailed flow-flow diagram of the hemodynamic, neuronal and related systems, which operate mechanically in AM or informationally in an FM mode, and operate based on the red blood cells, being paramagnetic iron heme, white cells, and lymphatic system. The processes are related to the Purkinje process as the master control of the neuronal FM or AM systems. The right side symbols in the three columns denote interconnections when the same symbols are used in different columns. Biological processes in the first column relate to each other based on, for example, metabolic activity, endocrine activity, and muscle activity. In the second column, the white cell system and immune system are related through the FM informational system and other processes such as those described herein. In the third column the FM and AM biological processing is related through major organs, neuronal process, mechanical muscles and related structures.

FIG. 8 denotes the relationship of the hypothalamus-pituitary axis (HPA) to some of the other biologic functions of the human body. The hypothalamus is connected by fibers to the pituitary of the cerebrum. Both ways from the heart are shown. The relationship of the cardiac system, to the adrenal glands, on the kidneys, and the vascular system is displayed.

FIG. 9a illustrates a DC bias polarity of the body and limbs. The upper regions of the body have positive polarity and the lower body and limbs have negative polarity.

Figure 9B:
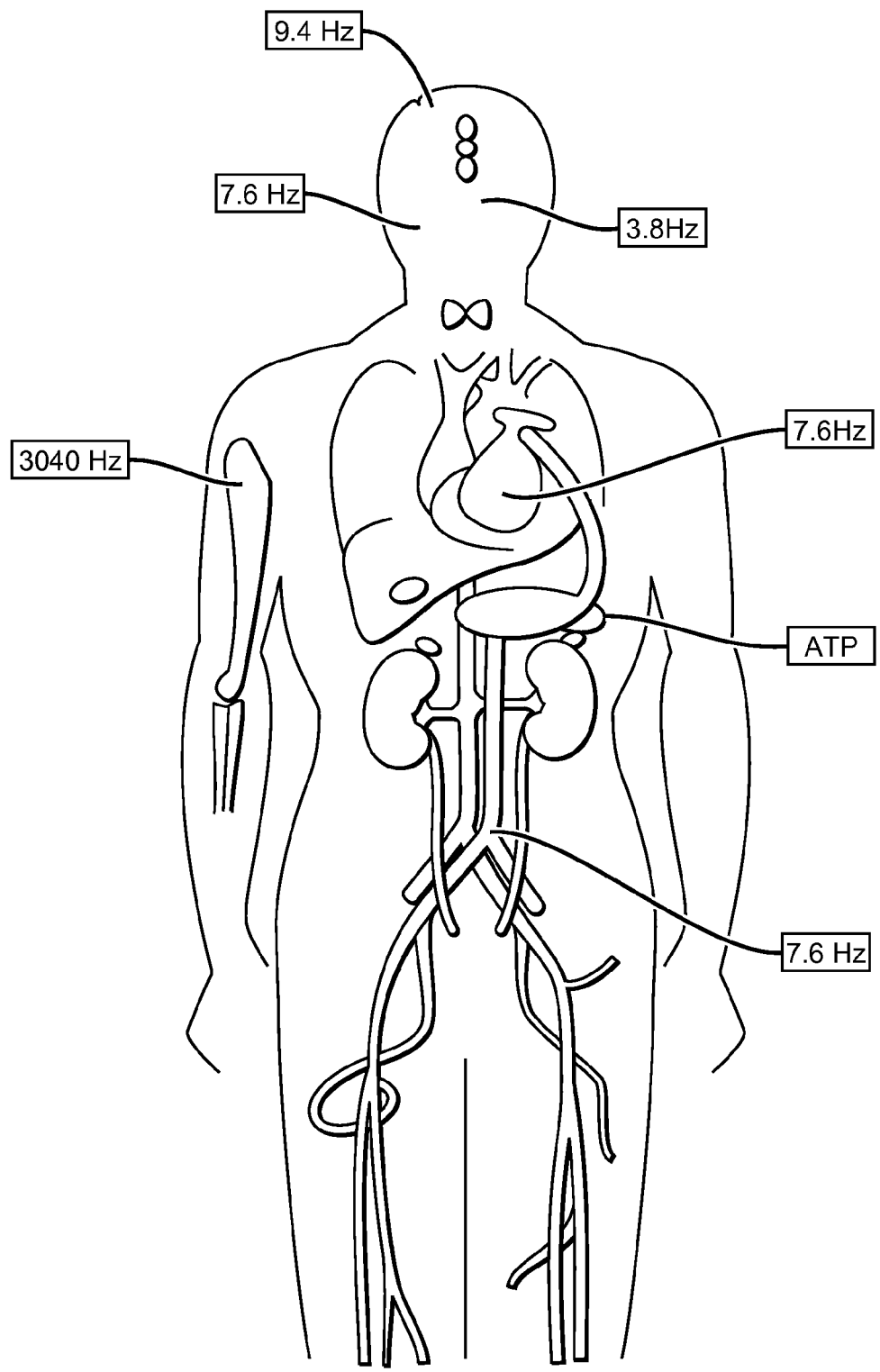
FIG. 9b displays a relationship between some of the primary organs of the human body and their primary frequency of oscillation response.

FIG. 9b illustrates relationships between some of the primary organs of the human body and their primary frequency of oscillation response. The cerebellum is responsive to approximately 9.4 Hz, which is near the alpha EEG power spectrum peak. The pineal, hypothalamus, pituitary, and Limbic system as a whole responds to approximately 3.8 Hz for relaxation and sleep. The cerebellum, cardiac system, and iliac bifurcation respond to approximately 7.6 Hz. The piezoelectric properties of the bones respond to approximately 3040 Hz.

As used herein, the term "approximately" means within 10%, inclusive.

FIG. 10a shows an ultra-low power transceiver that models communications between cells and a nervous system. An outside cell wall representation 536, a neutral charge of a cell, and a positively charged inside cell wall 532, are powered by a high impedance, low power, APT battery of a cell 574, inducing a frequency selective ATP Biologic Generator 512. The communication link is performed by a tuned circuit comprising or consisting of an inductor 510, and a capacitor 516, which provide a resonant loop and excites a resonator 513. This establishes an address for a cell. At the cellular level, DNA sequence commands can be received through a detector, an ideal biological switch 520, and a demodulator capacitor 525, and can be communicated to a cell through an output 560 at a precise frequency. Return communication can be modulated through a cell from an input 550 and modulated by ideal biological switch 518, then carried through a nervous system.

FIG. 10b shows the ATP synthesis and reactive process and complex in the outer membrane involving ATP 1010 cycling to and from ADP+$P_i$ 1012 (a phosphate group), through the phospholipid (protein) bilayer 1050. This mechanism passes a hydrogen ion $H^+$ through the membrane from a neutral pH of 7.2 1024 to the positively charged pH 5.5 1038 vesicle interior 1044 through protein bridges. ATP production is a 7.3 k Cal/mol energy reaction. The enzyme ATPase 1014 uncoats ATP for hydrolysis. Cytosol 1016 is a reactant protein channel transverse the cell wall as receptors (FM) and effectors (AM). Cytosol 1016 is part of the phosphate intake and release process. Dopamine 1022, through a hydrogen exchange 1021, moving outward through the membrane activates Dopamine 1040, and noradrenalin 1042 as neurotransmitters, both associated with wellbeing. Noradrenalin 1042 is also part of the adrenal process. Dopamine 1022 and noradrenalin 1042 are two of the catecholamines also synthesized in the adrenal cortex. Cholinergic and adrenergic processes are sensitive to ELF fields. The enzyme reductase 1126 causes hydrogen loss and electron production 1033 in the inner membrane. This cycle involves the exchange of ascorbic acid with semihydroascorbate 1028 exterior to the bi lipid layer. Passing through the membrane is electron production 1033 and internal membrane ascorbic acid balance 1032 as well as semidehydro-ascorbate. The cycle involves cytochrome $b_{561}$ which is also part of the Krebs cycle. A resonant group for frequency modulation occurs in the phospholipid (protein) bilayer 1050.

FIG. 11 illustrates the output of an embodiment of the inventive subject matter using the intermix of 7.6 Hz and 70.25 Hz for a one second trace and amplitude of 2 mV in the time domain.

FIG. 12 shows the time domain of the intermix of 7.6 Hz, 70.25 Hz, and 3040 Hz biologically active frequencies for a 100 ms sweep end to end with an amplitude of 8 V for one embodiment of the inventive subject matter.

Figure 13:
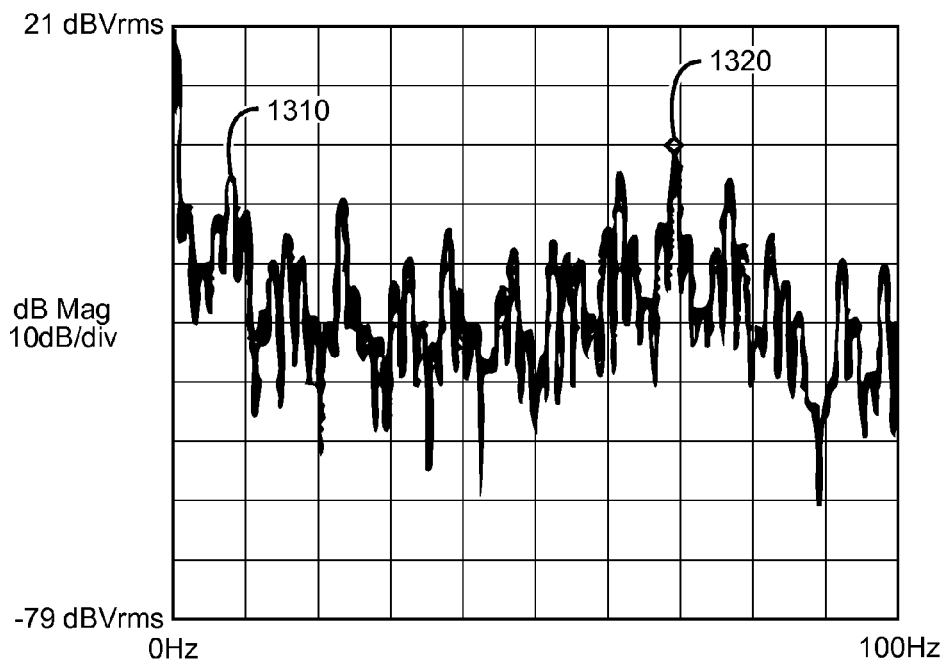
FIG. 13 displays the frequency domain from 0 to 100 Hz for the 7.6 Hz and 70.25 Hz intermix.

FIG. 13 shows the frequency domain from 0 to 100 Hz for the 7.6 Hz 1310 and 70.25 Hz 1320 intermix.

Figure 14:
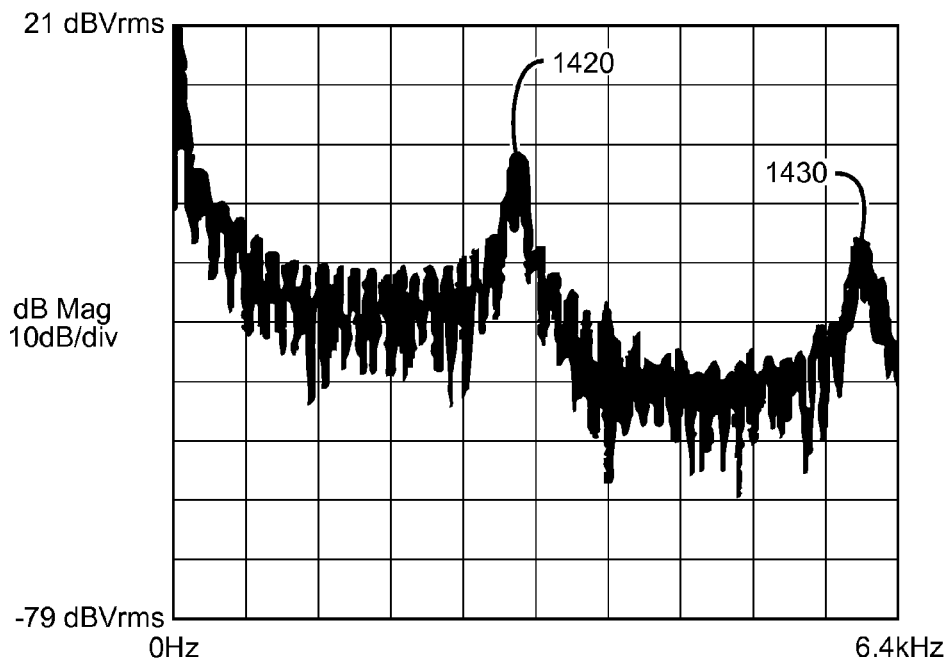
FIG. 14 shows the frequency domain of the 3040 Hz single frequency bone resonance carrier.

FIG. 14 shows the frequency domain of the 3040 Hz single frequency bone resonance carrier 1420 having a second harmonic frequency 1430. Denoted is the primary frequency of 3040 Hz as 1420 and second harmonic of 6080 Hz as 1430.

FIG. 15 displays some neurotransmitters and their pathways in the brain that are relevant to some embodiments of the inventive subject matter. The major brain organs affected by norepinephrine pathways are the neocortex, the thalamus, the hypothalamus, the cerebellar cortex, locus coerulems, the spinal cord, the hippocampus, and amygdala. The relevant pathways for dopamine are to the prefrontal cortex, nucleus accumbens, and particularly to the caudate nucleus and pulamen, the subinna nigra, the arculate nucleus, and amygdala. The pathways of serotonin in the brain are through the neocortex, the basal ganglia, and thalamus to the cerebellum, caudal raphe nuclei, to the spinal cord, rostal raphal nucleus, hippocampus, amygdala, and hypothalamus. Histamine flows to the neocortex, the basal ganglia, the thalamus, the cerebellum, the spinal cord is, the medulla, hippocampus, amygdala, and hypothalamus.

Figure 16C:
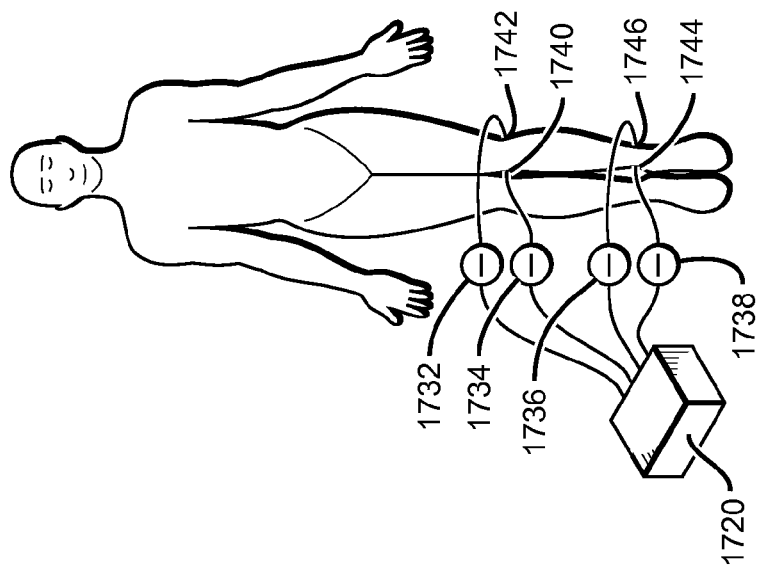
FIG. 16c shows the placement in the same embodiment as in FIG. 16b of other devices having negative DC biases.
Figure 16B:
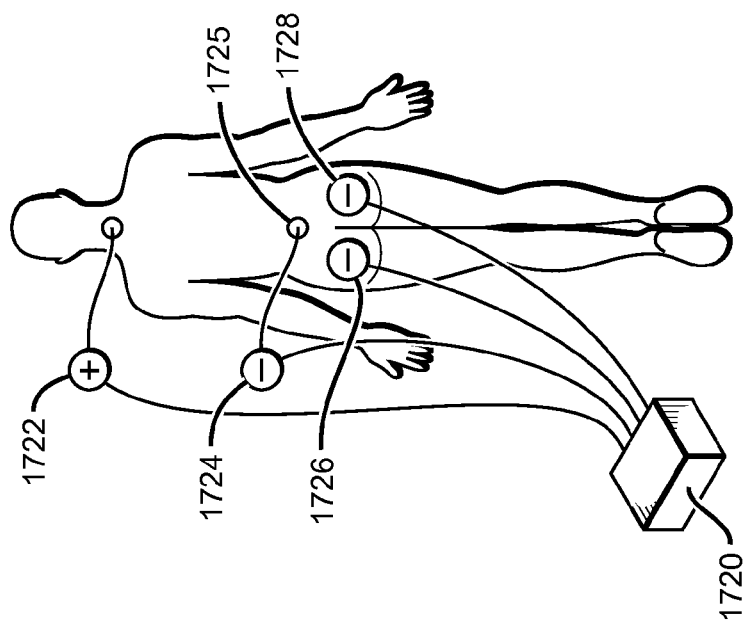
FIG. 16b shows an embodiment of the inventive subject matter, showing possible placement of devices having negative DC biases, placement of a device having a positive DC bias, and an electronic circuit generating the signals for the devices.
Figure 16A:
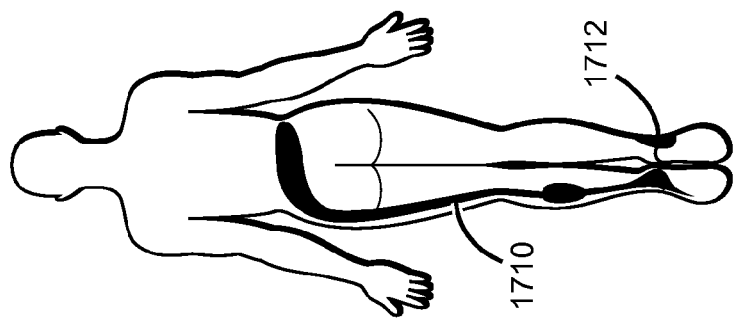
FIG. 16a illustrates a patient with chronic pain denoted by the darkened areas on the left side and on the right side.

FIG. 16a represents a patient with chronic pain denoted by the darkened area on the left side 1710 and on the right side 1712.

FIG. 16b shows how the patient of FIG. 16a can be treated using an embodiment of the inventive subject matter. The electronic circuit contained within a housing 1720 generates signals that are applied through coil emitters having a DC bias. Coil 1722 is positive and is placed over the C7 vertebra, a negative coil emitter 1724 is simultaneously or sequentially placed at or near L5 1725, and two other negative coil emitters at or near the great sciatic nerve injection points 1726 and 1728 for the proper allocated time of approximately 50 minutes.

FIG. 16c shows the next step in the treatment shown in FIG. 16b. The electronic circuit contained within a housing 1720 utilizes four coils 1732, 1734, 1736, and 1738 all having a negative DC bias, which are placed on the left leg of the patient at positions 1740, 1742, 1744, and 1746.

FIG. 17 is a graph illustrating data analysis of a pain rating scale of the patient from FIGS. 16a, 16b, and 16c before and after treatment with a method of the inventive subject matter. The vertical scale denotes level of pain on the VAS scale from no pain, 0, to the worst pain, 10, felt by the patient and the horizontal scale shows the number of pain reduction treatment sessions. The analytical trend for patient pain levels before treatment shows a slope of +0.1 and after treatment a slope of −1.33.

Figure 18A:
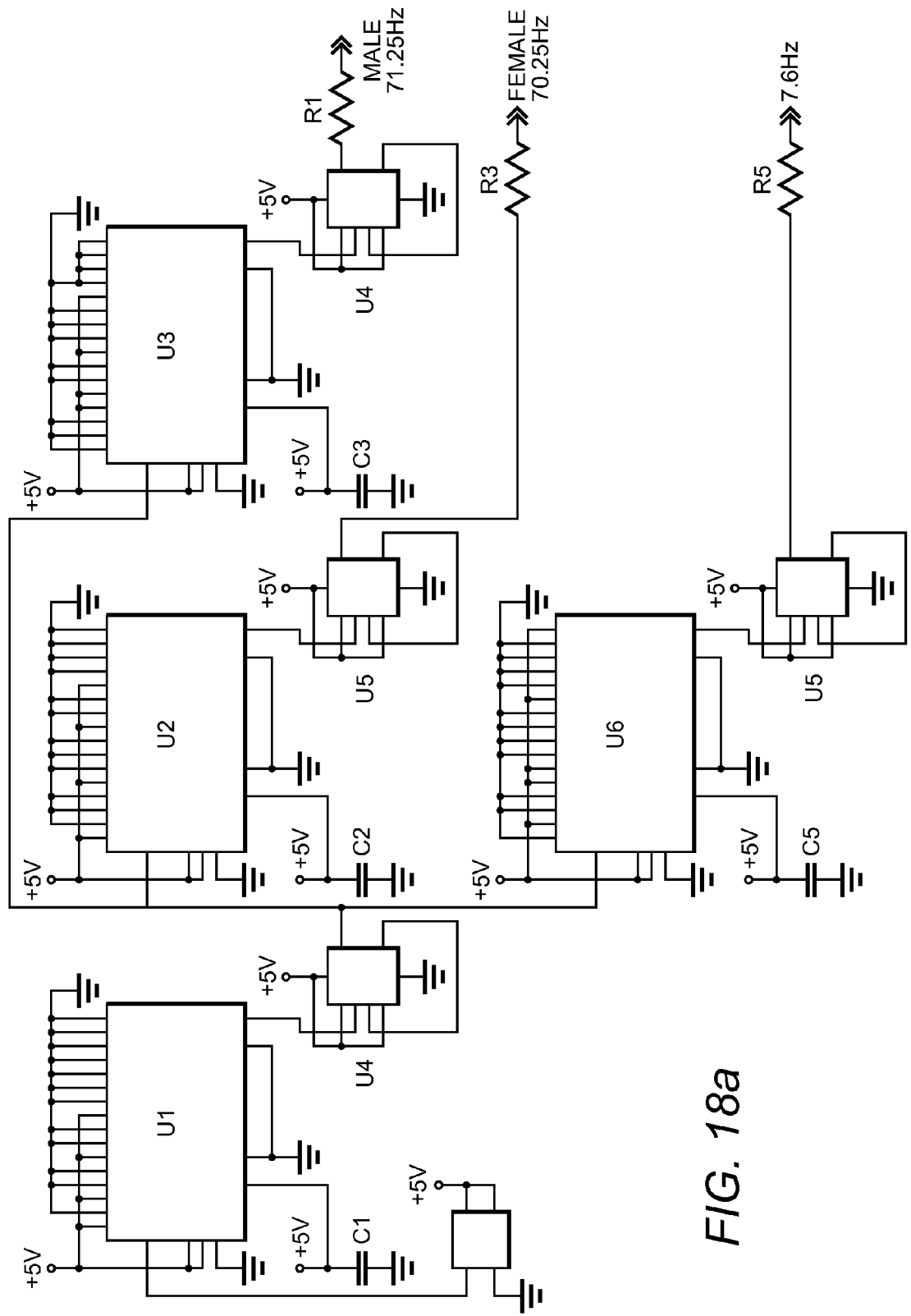
FIG. 18a shows a circuit diagram of an embodiment utilizing a voltage supply and frequency dividers to generate a 7.6 Hz signal having an approximate 50% duty cycle, and 70.245 Hz and 71.25 Hz signals having an approximate 25% duty cycle.

FIG. 18a shows a circuit diagram of an embodiment of the inventive subject matter wherein a voltage supply and frequency dividers are configured to be able to generate the 7.6 Hz signal having an approximate 50% duty cycle, and the 70.245 Hz and 71.25 Hz signals having an approximate 25% duty cycle. The clock timing circuit is powered by a regulated 5 V source. This supply voltage powers the master clock and a series of high speed frequency dividers. A master clock set to 32 MHz derives the common core frequency. The frequency driving the dividers then divides the clock into three timing frequencies. Frequencies are gender specific and must be mixed correctly. The frequencies are buffered and coupled to the Modulator Drive Control through the low impedance of 100 ohms. This achieves a square wave drive voltage (4.8 volts) from all output signals.

Figure 18B:
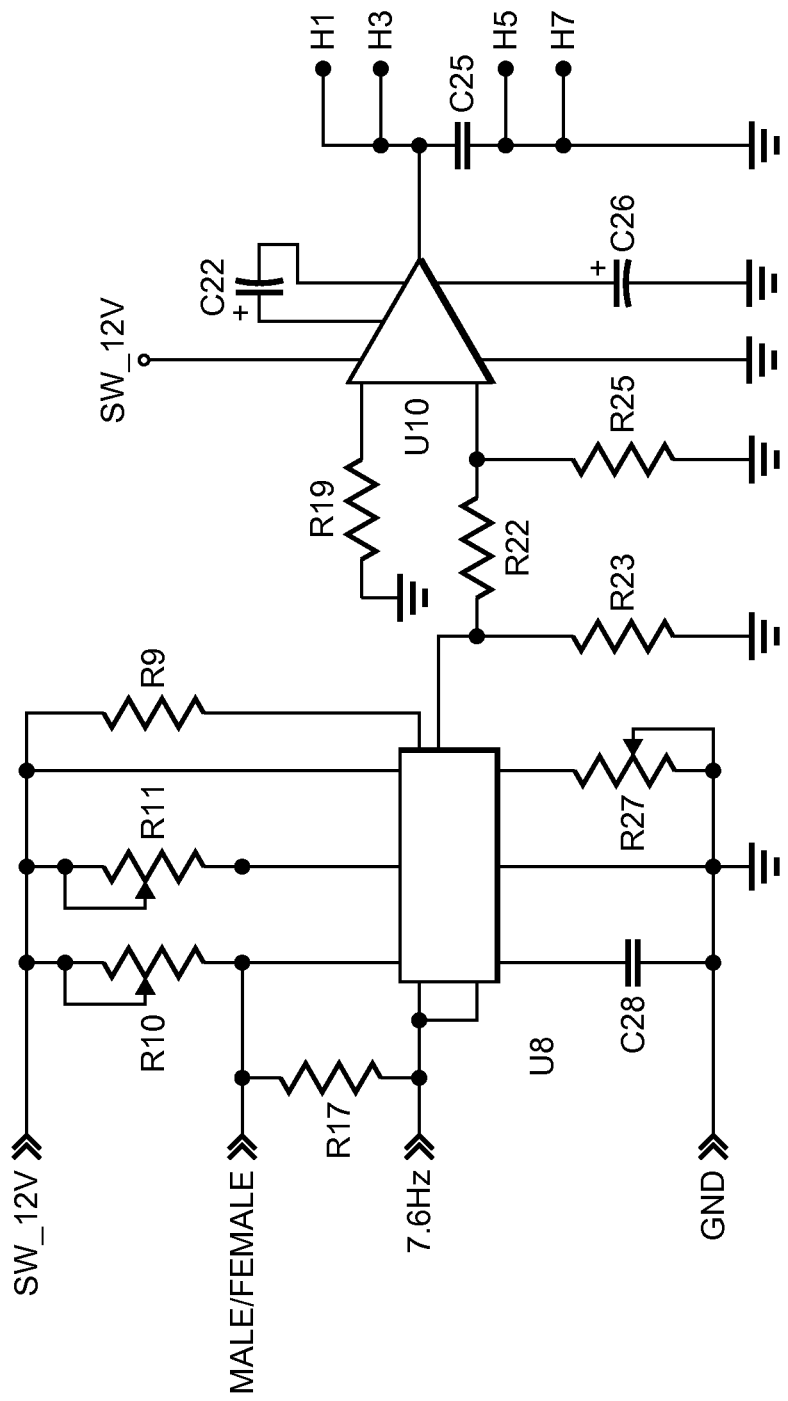
FIG. 18b shows a circuit diagram of an embodiment that generates a triangle waveform having a frequency of 3040 Hz with an approximate 33% duty cycle.

FIG. 18b shows a circuit diagram of an embodiment of the inventive subject matter displaying a triangle wave form generator for an initial oscillator frequency of 3040 Hz with about a 33% duty cycle backwards ramp wave. An intermix modulator of the three frequencies goes into the proper inductive lead to the coils which are applied to a patient. The frequency is set by R27 and timing capacitor C28. The triangle waveform is asymmetric, the leading ramp is 33% of the duty cycle, and the trailing ramp is 66%. Symmetry is set by R11 and the inversion is set by R10. The timing sequence then selectively modulates the duty cycle. R17 intermixes both high and low timing frequencies and drive the frequency modulator. The timing sequence also modulates the oscillator frequency by 10% centered on the initial 3040 Hz setting. A variable gain amplifier is gain dependent on signal density producing a cascade signal ringing. This signal is delivered to a target area by a number of coils to provide direct magnetic stimulation to nerves and soft tissues.

Figures 1, 18C:
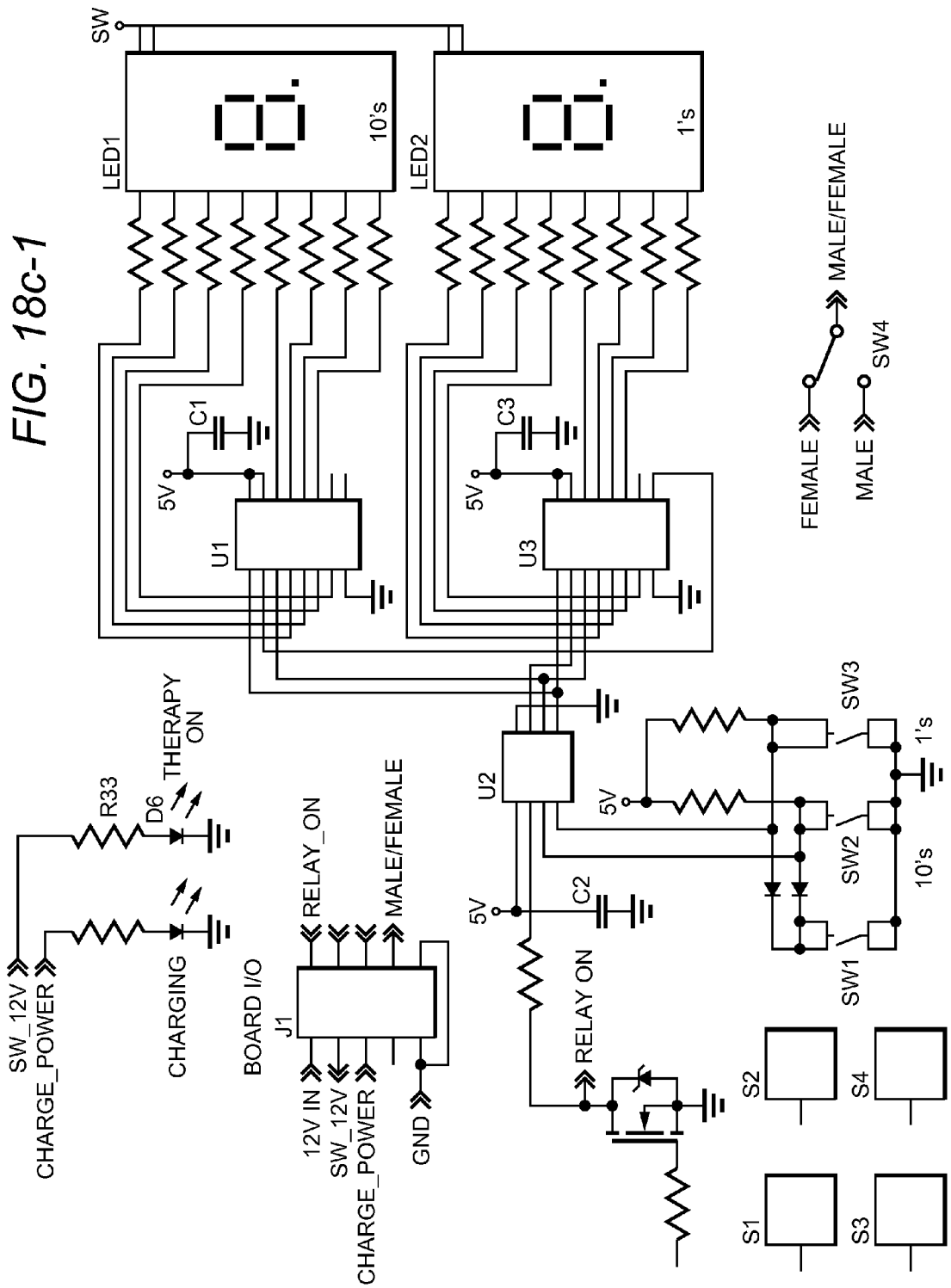
Figures 2, 18C:
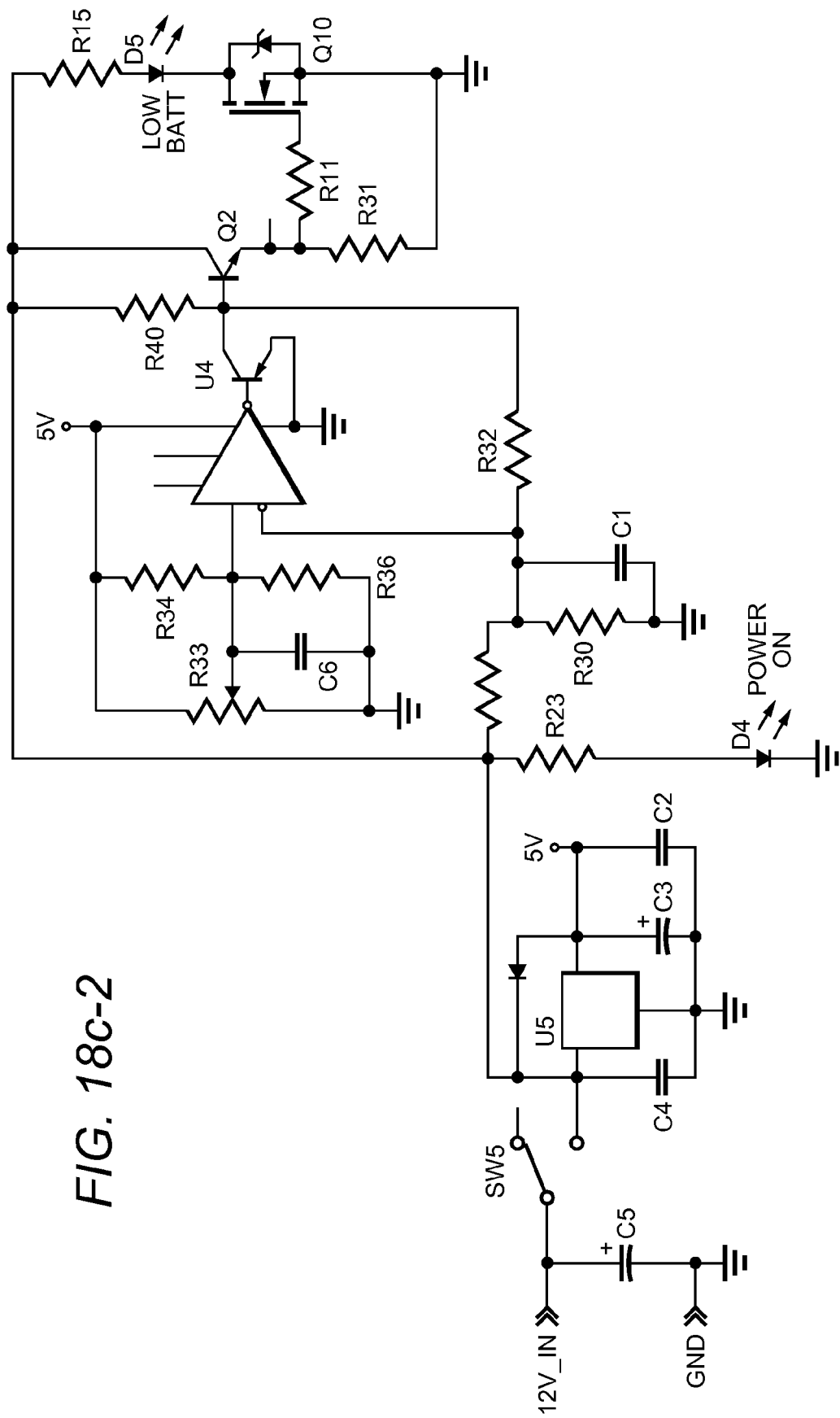

FIG. 18c1-2 shows a circuit diagram of an embodiment of the inventive subject matter that can be used as a therapy countdown timer with power switching controls. Power switch SW5 turns on the non-invasive pain device as indicated by the power LED D4, and current limit resistor R23. Battery condition is determined by comparator U4 and associated components as a precision threshold latch and performs the low battery lockout function and is indicated by low battery LED D5, also disables control line output with a clamp transistor Q10, and associated components R15 and R11. Power regulator U5 providing 5 V to microprocessor U2, the timer and associated components, displays LED1 and LED2 and display drivers U1 and U3, along with programming switches SW2 and SW3 set the duration of treatment. Start switch SW1 begins the countdown timer and also supplies a control on voltage, 5 V to the (relay on) control line. This control line switches on relay K2, with Q10 and R30 providing 5 volt power U15 for frequency divider, and 12 volts for the modulator and output driver. Therapy on indicator LED D6 and current limit resistor R33 signal the device is active and will remain illuminated until timer has reached "00" time.

Figure 18D:
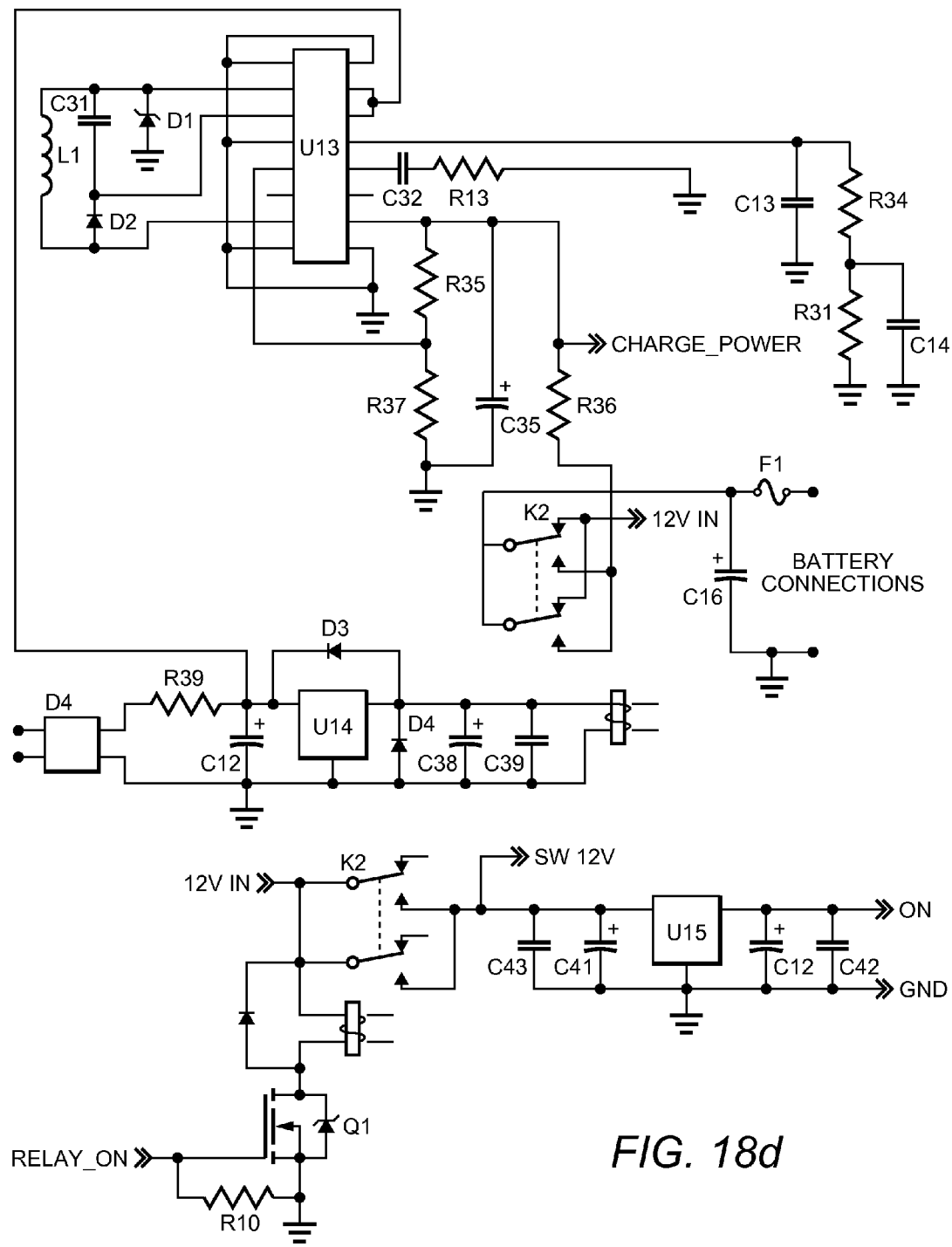
FIG. 18d shows a circuit diagram of a circuit used for power management in an embodiment of the inventive subject matter.

FIG. 18d shows a circuit diagram of an embodiment of the inventive subject matter that can be used for power management including regulators and battery charging. The battery is charged from a remote step down converter (18 V DC, 750 mA), powered from the line source. Charging the battery is indicated by a charging LED and current limiting resistor. The charging circuit is comprised of an input rectifier bridge and current limiting resistor—these components allow for proper input polarity and current limiting. Charger input voltage is detected by a relay and, when energized, begins the charging process. The charge controller and associated components form the charge switcher, and the regulation components control voltage. Timer components control the current charge rate. Rate of charge is set to 50 mA and recommended highest charger voltage not to exceed 20 V. The battery is protected by a fuse and resistor, and the capacitor suppresses noise.

FIG. 18e shows a circuit diagram taking the output of FIG. 18a from U4a pin 5 into S1 of FIG. 18e, and SW4 Fig. 18c1 into S2 of FIG. 18e. FIGS. 18c1-2 comprise the countdown circul and power supply switching controls as input to the circuit displayed in FIG. 18e. The output from the circuit in FIG. 18e connects to the output connectors and leads.

Table 1 displays some major theoretical properties of self organizing biological systems.

TABLE 1

1. Collective or mass motion of individual states, and coherent, non-dispersive low loss phenomena
2. Non-linear phenomena
3. Non-equilibrium open flux systems.
4. Coupled Resonance phenomena.
5. Dynamic or process-oriented phenomena.
6. Biologic information reception and transmission mechanisms.

Table 2 contains a model of informational channels in the human body and the operation of one embodiment of the inventive subject matter.

TABLE 2

1. Hydrodynamic "Standing wave" or soliton modes in the blood-cardiac system which comprise one of the informational channel in the human body. This channel operates by encoding magnetic field information utilizing the paramagnetic properties of the heme. Standing wave formation of about 7.6 Hz occurs in the iliac bifurcation.
2. Electric flow occurs as an informational and transformational channel in electrolytic saline solutions in the human body. Electrochemical and biochemical process can be induced by magnetic field impulses and carry information as potential differences and molecular bodies throughout the biological system.
3. The current flow in the neuronal pathways (CNS, PNS, etc.) also can be affected by pulsed magnetic fields, which induce current flows, and comprises what is considered the primary informational system of the body. These systems act as LRC tank circuits.
4. The piezoelectric spike wave response in bone can induce current flow in the system and introduces crystal activated current flow informational . components
5. The diode action of the Purkinje cell processes in the cerebellum and heart comprise a key organizing system in the human body's information channels.
6. Multiple coupled equations which describe the various informational and process channels of the human body. The coupling constant of the nonlinear terms of the coupled differential equations represents a recoherence term in which dispersive losses in the informational channels are overcome. This coupling term is expressible in terms of the soliton wave properties.

Table 3 presents the effective frequencies and tolerances used in an embodiment of the inventive subject matter derived from in vivo and in vitro experimentation of the fundamental resonances of the body's informational system. Bandwidths are found to be about a factor of four of their fundamental base frequencies. Duty cycles and wave forms are also given as well as the external field intensity at the skin surface to activate the associated biologic system, which is also listed. Some attenuation occurs as the field output of this embodiment penetrates deeply into tissues. Proper design features are constructed so the magnetic field strength induces the proper current and voltages at the proper site for correct tissue response and normalization. Because high frequencies can ride on and modulate lower frequencies, it is possible that such signaling processing can carry sufficient information content in order to effect and normalize and correct biologic processing to eliminate pain and enhance health.

TABLE 3

| Frequency and Tolerance (Hz) | Band Width (Hz) | Duty Cycle (%) | Dominate Wave Form | Intensity (G) | Primary Biologic System and Effects |
|---|---|---|---|---|---|
| 3.2 + .6 3.2 - .1 | 12.8 | 25-50 | Triangle or Square | .1 mG to 2 G | Relaxation and Sleep |
| 7.6 ± .02 | 30.4 | 50 | Square | 1.5 G to 3 G | Cerebellum, Cardiac, and Iliac Bifurcation, Hemodynamics |
| 9.41 ± .03 | 37.6 | 25-33 | Square | 1 uG to 1 mG | Cerebrum, Alpha wave enhancement (Improves brain |

TABLE 3-continued

| Frequency and Tolerance (Hz) | Band Width (Hz) | Duty Cycle (%) | Dominate Wave Form | Intensity (G) | Primary Biologic System and Effects |
|---|---|---|---|---|---|
| | | | | | function and reduces depression) |
| 70.25 ± .5 For females 71.25 ± .5 For males | 281 | 25 | Square | 5-50 G | CNS, PNS and Other Nervous Tissues |
| 647 ± 5 | 2589 | 33-50 | Pulsed Square and Triangle Intermix | .1 mG to .1 G | Cerebrum |
| 3040 ± 10 (Based on ½ wave value) | 12,160 | 33 | Triangle Ramp Wave | 5-50 G | Bone, Connective Tissues and Neuronal Processes |
| Full Wave Value 6080-7200 | 24,320-28,800 | 33 | Triangle Ramp Wave | 5-50 G | Bone and Collagen, Tendons and Ligaments |

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of treating a vertebrate organism, comprising:
    using at least one electronic circuit to produce a first signal having a first frequency, and a second signal having a second frequency that is different from the first frequency;
    using a first device having a positive direct current bias and coupled to the electronic circuit to target the first and second signals to a first portion of the organism in a manner that the signals are superimposed, and received at the first portion at physiologically acceptable intensities and duty cycles such that the signals entrain a first target tissue of the organism;

wherein the first portion comprises brain tissue; and
using a second device having a negative direct current bias and coupled to the electronic circuit to target the first and second signals to a second portion of the organism different from the first portion in a manner that the signals are superimposed, and received at the second portion at physiologically acceptable intensities and duty cycles such that the signals entrain a second target tissue of the organism.

2. The method of claim 1, wherein the vertebrate organism is a human.

3. The method of claim 1, wherein the first and second signals are selected to produce a plurality of intermodulated additional signals.

4. The method of claim 1, wherein the devices emit the first and second signals as a magnetic field.

5. The method of claim 1, wherein the devices emit the first and second signals as electromagnetic fields.

6. The method of claim 1, wherein the second frequency is selected from the list consisting of 7.6 Hz +/−2 Hz., 70.25 Hz +/−0.25 Hz, 71.25 Hz +/−0.25 Hz, and 3040 Hz +/−10 Hz.

7. The method of claim 1, wherein the first device and second device compose a multi-coil array.

8. The method of claim 1, further comprising applying the first and second signals for a duration of time sufficient to enhance relaxation and sleep.

9. The method of claim 1, further comprising targeting the first and second signals to affect Purkinje cells of the living being, and wherein the first frequency is 3.2 Hz +0.6/−0.1 Hz.

10. The method of claim 1, wherein the steps of using the first device and using the second device occur concurrently.

11. The method of claim 1, wherein the first frequency is 3.2 Hz +0.6/−0.1 Hz, and is applied at an approximately 50% duty cycle.

12. The method of claim 1, wherein the second frequency is 3040 Hz +/−10 Hz, and is applied at an approximately 25% duty cycle.

13. The method of claim 1, wherein the first target tissue is brain tissue, and wherein the first frequency is 9.41 +/−2 Hz.

14. The method of claim 1, further comprising administering the first and second signals to enhance sleep, and wherein the first frequency is 3.2 Hz +0.6/−0.1 Hz.

15. The method of claim 1, further comprising using at least one of the first and second devices to target at least one of the first and second target tissues with a third signal having a third frequency, wherein none of the first, second and third signals is phase locked in the tissue.

16. The method of claim 15, wherein the first frequency is 3.2 Hz +0.6/−0.1 Hz , the second frequency is 3040 Hz +/−10 Hz, and the third frequency is 9.41 +/−2 Hz.

17. The method of claim 1, wherein the first frequency is 3.2 Hz +0.6/−0.1 Hz and is applied at a duty cycle between 25-50%.

18. The method of claim 1, wherein the second frequency is 3040 Hz +/−10 Hz, and is applied at an approximately 33.3% duty cycle.

19. The method of claim 1, further comprising applying the first and second signals for a duration of time and at frequencies sufficient to induce a biochemical process that enhances relaxation and sleep.

20. The method of claim 19, wherein the biochemical process comprises producing at least one of a Serotonin and a Dopamine.

* * * * *